United States Patent
Kimura et al.

(10) Patent No.: US 8,066,682 B2
(45) Date of Patent: Nov. 29, 2011

(54) EYE DROPS CONTAINER

(75) Inventors: Takahito Kimura, Toyama (JP);
Kazuhide Maeda, Higashimurayama (JP); Nobuyuki Hanai, Kawagoe (JP);
Tomoyuki Watanabe, Kanazawa (JP)

(73) Assignees: Teika Pharmaceutical Co., Ltd., Toyama-shi (JP); Toyo Aerosol Industry Co., Ltd., Tokyo (JP); Shinko Chemical Co., Ltd., Kanazawa-shi (JP)

( * ) Notice: Subject to any disclaimer, the term of this patent is extended or adjusted under 35 U.S.C. 154(b) by 465 days.

(21) Appl. No.: 12/377,064

(22) PCT Filed: Aug. 10, 2007

(86) PCT No.: PCT/JP2007/065688
§ 371 (c)(1),
(2), (4) Date: Feb. 10, 2009

(87) PCT Pub. No.: WO2008/018579
PCT Pub. Date: Feb. 14, 2008

(65) Prior Publication Data
US 2010/0174247 A1   Jul. 8, 2010

(30) Foreign Application Priority Data

Aug. 11, 2006   (JP) ................................ 2006-219068

(51) Int. Cl.
*A61M 11/00* (2006.01)

(52) U.S. Cl. ..................... 604/298; 128/200.23; 251/89; 222/402.11

(58) Field of Classification Search ........... 604/294–302
See application file for complete search history.

(56) References Cited

U.S. PATENT DOCUMENTS 2,673,661 A * 3/1954 Barton .......................... 222/212
(Continued)

FOREIGN PATENT DOCUMENTS

GB       2058229 A * 4/1981
(Continued)

OTHER PUBLICATIONS

Translation of JP 45-012021.*
Machine translation of JP 2003-190255.*

*Primary Examiner* — Jacqueline Stephens
*Assistant Examiner* — Paula Craig
(74) *Attorney, Agent, or Firm* — Oblon, Spivak, McClelland, Maier & Neustadt, L.L.P.

(57) ABSTRACT

An eye drops container including a container body filled with a drug solution along with a pressurized gas and including a valve mechanism discharging a fixed amount of drug solution; a nozzle member coupled with a stem for open operation of the valve mechanism and including a drug solution drop nozzle; an operating member including an operating piece and attached to the container body; a guide member contained in the operating member and guiding the nozzle member in the axial direction; and a ball contained in the guide member. The nozzle member includes an outer flange for suspending a skirt on the lower surface thereof; the guide member includes a ring-like bottom groove into which the forward end of the skirt enters; and the ball falls into the bottom groove in an upright state to block the open operation of the valve mechanism, and falls onto the outer flange in an inverted state to permit the open operation of the valve mechanism.

6 Claims, 7 Drawing Sheets

(A)

(B)

U.S. PATENT DOCUMENTS

| | | | | |
|---|---|---|---|---|
| 3,542,254 A | * | 11/1970 | Davenport et al. | 222/402.19 |
| 3,788,523 A | * | 1/1974 | Thomas | 222/153.04 |
| 4,122,979 A | * | 10/1978 | Laauwe | 222/633 |
| 4,978,038 A | * | 12/1990 | Sullivan | 222/402.19 |
| 4,981,479 A | * | 1/1991 | Py | 604/302 |
| 5,038,964 A | * | 8/1991 | Bouix | 222/153.04 |
| 5,803,319 A | * | 9/1998 | Smith et al. | 222/402.19 |
| 6,047,946 A | * | 4/2000 | Kolanus | 251/89 |
| 6,427,684 B2 | * | 8/2002 | Ritsche et al. | 128/200.23 |
| 7,635,070 B2 | * | 12/2009 | Cohen et al. | 222/162 |

FOREIGN PATENT DOCUMENTS

| | | |
|---|---|---|
| JP | 36 4886 | 3/1961 |
| JP | 45 12021 | 5/1970 |
| JP | 3 126887 | 12/1991 |
| JP | 2003 154295 | 5/2003 |
| JP | 2003 190255 | 7/2003 |
| JP | 2006 103750 | 4/2006 |

* cited by examiner (A)

(B)

EYE DROPS CONTAINER

TECHNICAL FIELD

This invention relates to an eye drops container which can drop a drug solution only in an inverted state for ocular instillation.

BACKGROUND ART

An eye drops container obtained by combining a container body to be filled with a drug solution along with a pressurized gas and an operating member with an operating piece to be provided in the container body has heretofore been known (Patent Document 1).

A valve mechanism for discharging a fixed amount of the drug solution is incorporated into the container body of the eye drops container, and a nozzle member interlocked with the hinge type operating piece of the operating member is coupled with a stem for open operation of the valve mechanism. Also, the drug solution from the container body is discharged to the nozzle member via the hollow stem when the open operation of the valve mechanism is performed by pressing the stem in an axial direction, so that the drug solution is dropped from a drop nozzle formed on the nozzle member. The eye drops container having such mechanism has great advantages that the drug solution inside the container body is free from contamination since an ambient air does not flow into the container body when the drug solution is discharged and that it is unnecessary to add any antiseptic agent.
Patent Document 1: JP-A-2003-190255

DISCLOSURE OF THE INVENTION

Problem that the Invention is to Solve

With such conventional technique, it is possible to perform the open operation of the valve mechanism via the operating member irrespective of a posture of the container body. Therefore, when an erroneous open operation is performed in an upright state, only the pressurized gas of the container body is discharged to cause a reduction in internal pressure of the container body, thereby making it impossible to discharge the drug solution due, resulting in a problem of raising a risk of wasting the drug solution.

Accordingly, in view of the problem of the above-described conventional technique, an object of the present invention is to provide an eye drops container capable of allowing an open operation of a valve mechanism only in an inverted state by combining an operating member with an operating piece, a guide member, and a ball. Another object of this invention is to provide an eye drops container which can be used more comfortably by downsizing shapes of the operating member and a nozzle member.

Means for Solving the Problem

In order to attain the above-described object, this invention provides an eye drops container comprising a container body being filled with drug solution along with a pressurized gas and incorporating a valve mechanism for discharging a fixed amount of drug solution; a nozzle member coupled with a stem for open operation of the valve mechanism and having a drug solution drop nozzle; an operating member provided with an operating piece and attached to the container body; a guide member contained in the operating member and guiding the nozzle member in an axial direction; and a ball contained in the guide member, wherein the nozzle member has an outer flange for suspending a skirt on the lower surface thereof; the guide member has a ring-like bottom groove into which the forward end of the skirt enters; and the ball falls into the bottom groove in an upright state to block the open operation of the valve mechanism and falls onto the outer flange in an inverted state to permit the open operation of the valve mechanism.

Also, in the present invention, it is possible to form on the operating piece axially symmetrical projections for pressing the outer flange, and it is possible to provide the operating member with a detachable cap for containing the nozzle member and the operating member.

Further, in the present invention, it is preferable that the drop nozzle suppresses the drug solution remaining inside to a minimum amount.

Advantage of the Invention

According to the present invention, it is possible to perform the open operation of the valve mechanism only in the inverted state, and there is no risk for an erroneous open operation of the valve mechanism in the upright state. Since the fixed amount of the drug solution is discharged to the drop nozzle of the nozzle member via the hollow stem to be dropped as a droplet from the drop nozzle when the open operation of the valve mechanism is performed in the inverted state, a problem that only the pressurized gas inside the container body is discharged due to the erroneous open operation will never occur.

In the present invention, it is possible to correctly drive the stem of the valve mechanism in the axial direction via the nozzle member by forming the axially symmetrical projections for pressing the outer flange on the operating piece, thereby eliminating the risk of applying an unnecessary bending stress to the stem.

Further, in the present invention, it is possible to prevent a harmfully large amount of the drug solution from being dropped by so designing the drop nozzle as to suppress the drug solution remaining in a nozzle pore to the minimum amount.

DESCRIPTION OF REFERENCE NUMERALS

Figure 1:
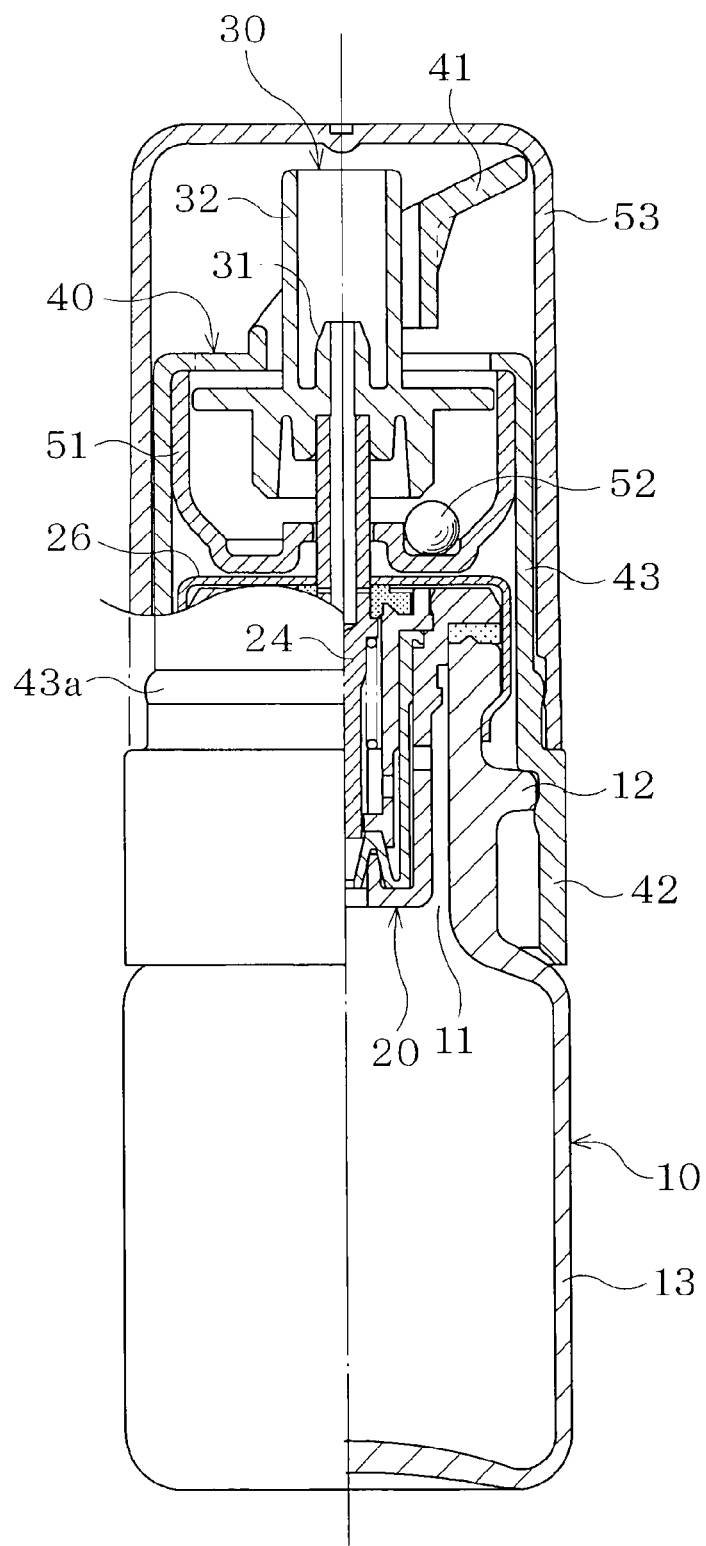
[FIG. 1] A partially cut-away view showing an overall structure according to one embodiment of the eye drops container of the present invention.

10: container body
20: valve mechanism
24: stem
30: nozzle member
31: drop nozzle 33: outer flange
34: skirt
40: operating member
41: operating piece
41b: projection
51: guide member
51a: bottom groove
52: ball
53: cap
54: partition wall
55: slit

BEST MODE FOR CARRYING OUT THE
INVENTION

Hereinafter, a preferred mode of embodiment of the present invention will be described in conjunction with the drawings.

FIG. 1 is a partially cut-away view showing an overall structure of an eye drops container according to one embodiment of the present invention. As shown in FIG. 1, the eye drops container is provided with a container body 10 for incorporating a valve mechanism 20, a nozzle member 30 having a drop nozzle 31, an operating member 40 with an operating piece 41, a guide member 51, and a ball 52. The operating member 40 is provided with a cap 53.

The container body 10 is filled with a drug solution (not shown) along with a pressurized gas. The container body 10 is formed from a transparent material and has a bottomed cylindrical shape so that an amount of the drug solution is confirmed from outside. On the container body 10, an outer flange 12 is formed around an outer periphery of an opening part 11 of an upper part, and a barrel part 13 is formed on a lower part. The operating member 40 is attached to the upper part of the container body 10 by engagement of a base part 42 with the outer flange 12, the base part 42 having a substantially same outer diameter with the barrel part 13.

Figure 2:
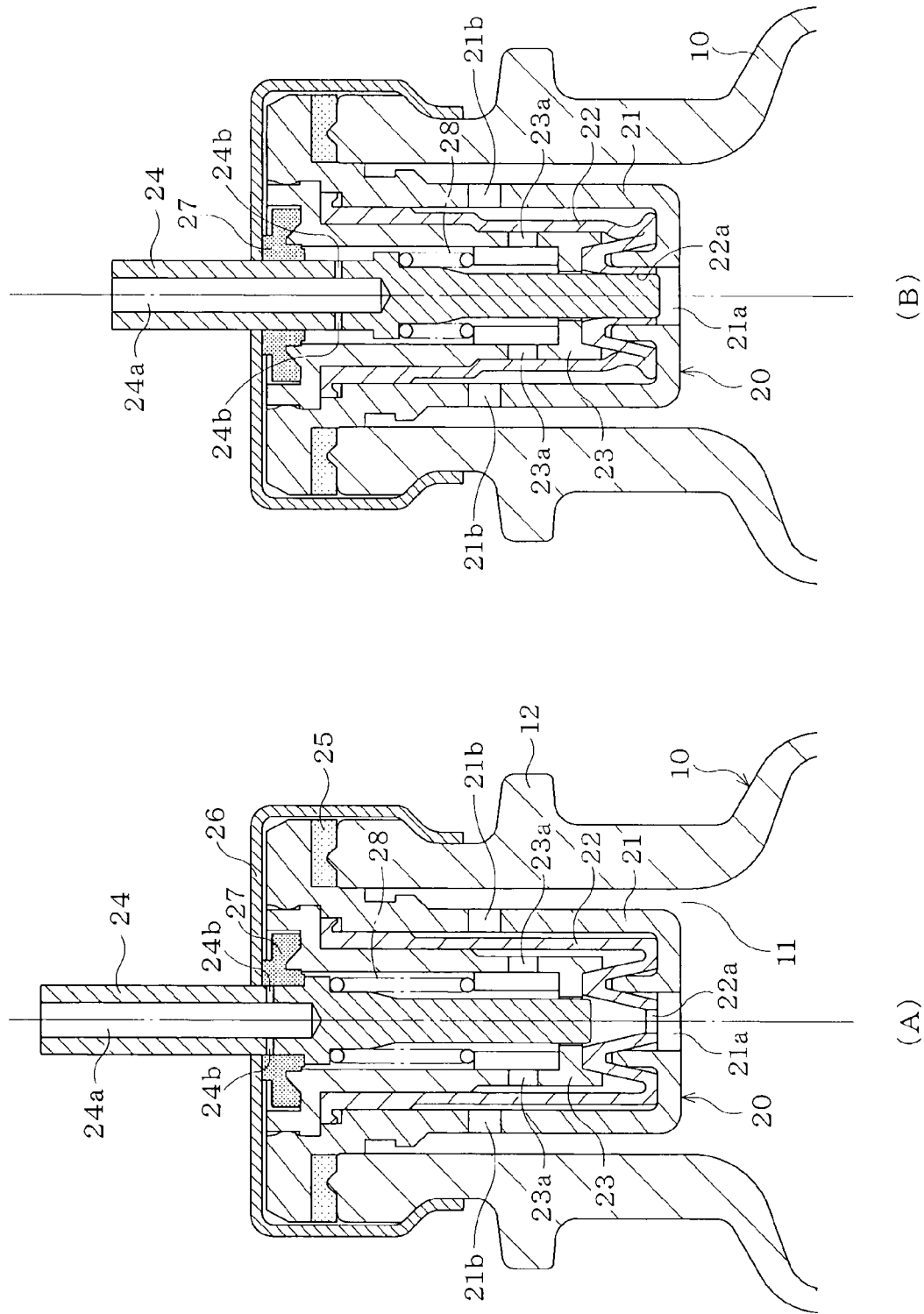
[FIG. 2] An enlarged sectional view for explaining an operation of a valve mechanism part.

The valve mechanism 20 shown in FIG. 2 for discharging a fixed amount of the drug solution is attached to the opening part 11 of the container body 10.

The valve mechanism 20 is formed by coaxially incorporating a deformable tank 22, a guide cylinder 23, and a stem 24 in this order into a case 21 having a bottomed cylindrical shape. The case 21 is crimped to an upper end of the opening part 11 via a sealing packing 25 and a mount plate 26. A pore 21a having an inward rib is formed on the center of a bottom part of the case 21, and a plurality of pores 21b, 21b, and the like are formed on a lateral surface. The tank 22 inside the case 21 is formed from a flexible material, and a downward pore 22a is formed on a bottom part of the tank 22 in such a fashion as to fit the rib around the pore 21a of the case 21. An upper end part of the guide cylinder 23 is held by the case 21 together with an upper end part of the tank 22. The guide cylinder 23 is provided with a plurality of pores 23a, 23a, and the like formed on a lower half part having a smaller outer diameter than an upper half part.

The stem 24 is slidably incorporated into the guide cylinder 23 via the sealing packing 27. The stem 24 projects longwise as penetrating upward through the sealing packing 27 and the mount plate 26 and biased upward via a spring 28 of the guide cylinder 23 to be retained via the sealing packing 27. A pore 24a is formed on the axial center in an upper half part of the stem 24, and the pore 24a is communicated with the outside via pores 24b and 24b having a very small diameter at a position of the sealing packing 27. A lower end part of the stem 24 downwardly penetrates through a bottom part of the guide cylinder 23 to face the pores 22a and 21a of the tank 22 and the case 21.

The valve mechanism 20 is brought into a state of FIG. 2(A) by an upward force of the spring 28 when an external force is not applied to the stem 24, so that the pores 24b and 24b of the stem 24 are closed via the sealing packing 27. Therefore, the pressurized gas inside the container body 10 fills inside and outside of the case 21, the tank 22, and the guide cylinder 23 via the pores 21a, 21b, 21b, 22a, 23a, 23a, and the like to prevent the tank 22 from being deformed. A sufficient space is defined at the penetration part of the stem 24 at the bottom part of the guide cylinder 23.

When the stem 24 is pressure-driven in the axial direction against the spring 28, a state shown in FIG. 2(B) is established, so that the pores 24b and 24b are opened below the sealing packing 27 to allow the inside of the guide cylinder 23 to communicate with the outside via the pores 24b, 24b, and 24a of the stem 24. Here, the inside of the tank 22 is also communicated with the outside via the pores 23a and 23a, and the flexible tank 22 is deformed in such a fashion as to closely contact the guide cylinder 23, whereby an inside volume is reduced. At this time, the pores 22a and 21a of the bottom parts of the tank 22 and the case 21 are closed since the lower end part of the stem 24 is inserted. Therefore, the valve mechanism 20 is capable of discharging a fixed amount of the pressurized gas corresponding to an amount of change of inner volume of the tank 22 from a tip of the stem 24 to the outside via the pores 23a, 23a, 24b, 24b and 24a.

Foregoing is the explanation of the process for the flow of the eye drop from the inside of the container 10 to the stem 24 in the container body incorporating the valve mechanism of the eye drops container of the present invention in the case where the pressurized gas fills around the valve mechanism 20 inside the container body 10, but the stem 24 cannot be pressed into the guide cylinder 23 in the upright state in this invention. That is to say, the valve mechanism 20 is capable of pressing the stem 24 into the guide cylinder 23 only when the whole part is in the inverted state, and, by the open operation of the stem 24 by pressing in the axial direction, it is possible to discharge a fixed amount of the drug solution inside the container body 10 from the tip of the hollow stem 24 via the pore 24a at the axial center of the stem 24. A nozzle mechanism that enables the discharge of the drug solution only in the inverted state will be described below.

Figure 3:
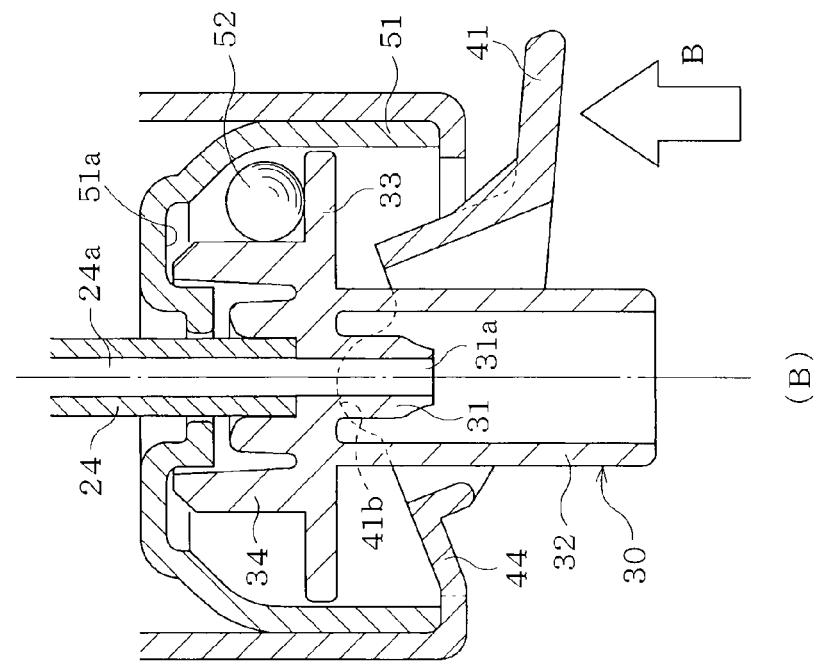
[FIG. 3] An enlarged sectional view for explaining an operation of the nozzle mechanism.
Figure 3:
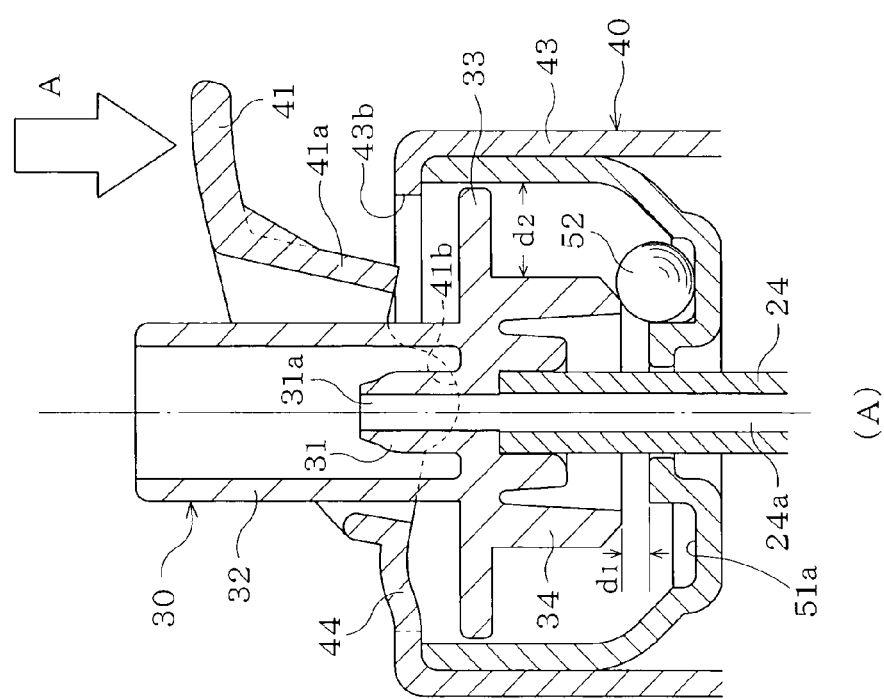
Figure 4:
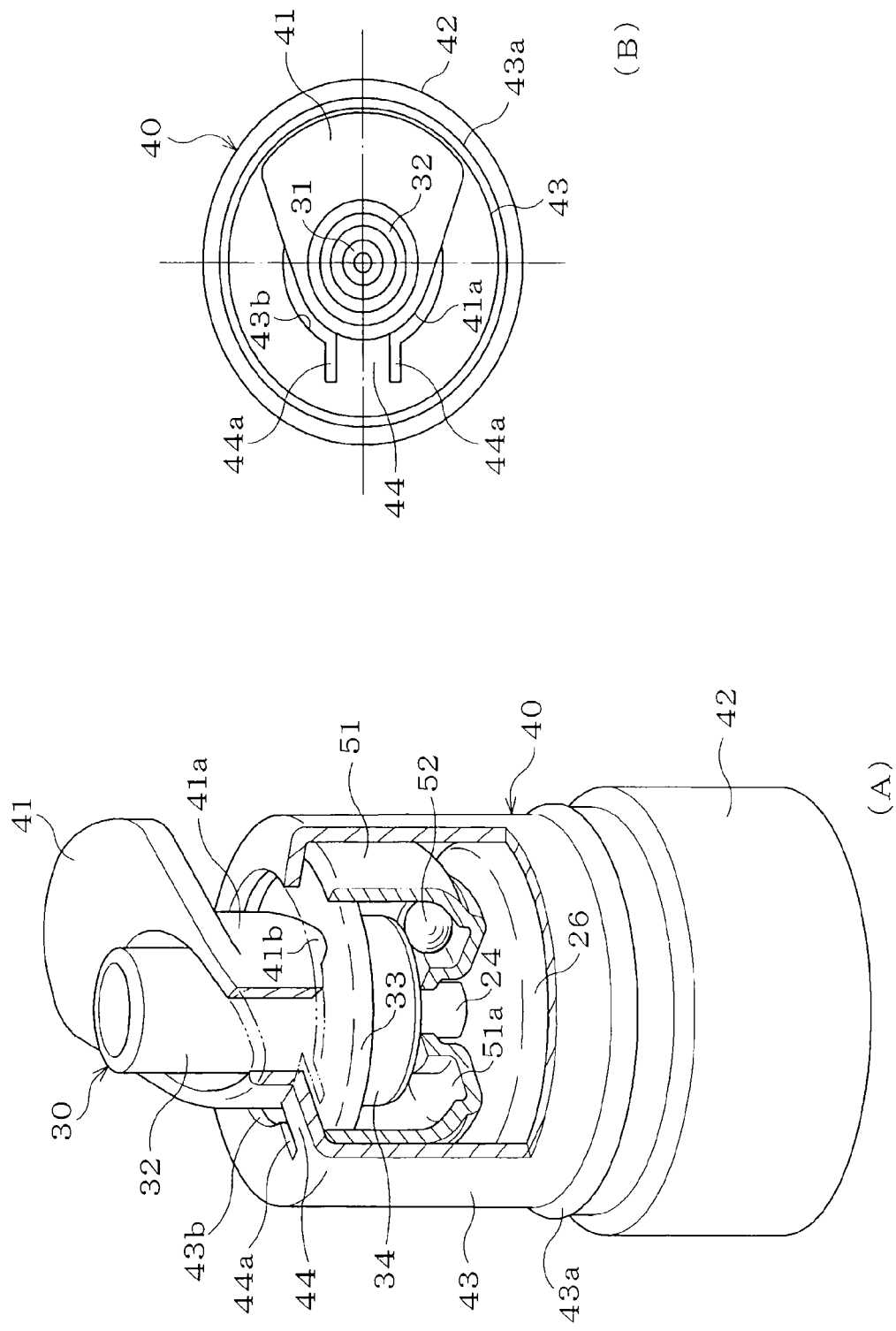
[FIG. 4] A partially cut-away perspective view and a plane view showing the nozzle mechanism.

FIG. 3 is a sectional view showing the nozzle mechanism, FIG. 4 (A) is a partially cut-away perspective view of FIG. 3, and FIG. (B) is a plane view of FIG. 3. As shown in FIG. 3, the nozzle member 30 is contained in a main body part 43 in the upper part of the operating member 40 together with the guide member 51 and coupled with the tip of the stem 24 of the valve mechanism 20. The nozzle member 30 is formed of a short drop nozzle 31 and a long outer cylinder 32 that are coaxial to each other and projected above the outer flange 33 as well as of a skirt 34 suspending from a lower surface of the outer flange 33. A nozzle pore 31a on the axial center of the drop nozzle 31 is continued from the pore 24a on the axial center of the stem 24, and a lower end of the skirt 34 is thinned by obliquely notching an outer surface. Also, the operating member 40 has such a structure that the main body part 43 having a smaller diameter is formed on a base part 42 having a larger diameter and the operating piece 41 extending obliquely upward is integrally molded on an upper surface of the main body part 43.

An engagement rib 43a for the cap 53 is formed on a lower outer periphery of the main body part 43. Also, a cylindrical base 41a having a partial notch is provided on the operating piece 41 that allows an outer cylinder 32 of the nozzle member to upwardly penetrate therethrough, and downward projections 41b and 41b are axially symmetrically formed on a lower end of the base 41a. Note that only one of the projections 41b is shown in FIG. 4(A). Further, a pore 43b having a sufficiently larger diameter than the base 41a is formed on an upper surface of the main body part 43. Also, the base 41a is connected to the upper surface of the main body part 43 via an elastic tongue piece 44 defined by notches 44a and 44a that are in a direction reverse to the operating piece 41.

As shown in FIG. 3(A), the guide member 51 is upwardly inserted into the main body part 43 of the operating member 40 from below to reach the mount plate 26 of the valve mechanism 20. The guide member 51 is in the form of a bottomed cup, and a bottom groove 51a in the form of a ring is formed around the stem 24 at the bottom part that allows the stem 24 to upwardly penetrate therethrough. The bottom groove 51a is in the form of a shallow upward channel, and an outer diameter of an inner side wall of the bottom groove 51a is in conformity with an inner diameter of the skirt 34 of the nozzle member 30. The outer flange 33 of the nozzle member 30 is contained in an upper part of the guide member 51, and the guide member 51 guides the nozzle member 30 in the axial direction via the outer flange 33.

One or more balls 52 is/are contained in the bottom groove 51a of the guide member 51. The ball 52 may be formed from an appropriate material such as stainless steel, glass, and hardened plastic. A distance d1 between the lower end of the skirt 34 and an uppermost part of the bottom part of the guide member 51 is sufficiently smaller than a diameter of the ball 52 in a stationary state in which the stem 24 is not pressed, and a gap d2 between an outer surface of the skirt 34 and an inner surface of the guide member 51 is sufficiently larger than the diameter of the ball 52 along a whole path from the bottom of the bottom groove 51a to the lower surface of the flange 33.

Further, the nozzle mechanism of the eye drops container of the present invention may be covered with the cap 53. The cap 53 is detachably attached to the operating member 40 via the engagement rib 43a in such a fashion as to contain the nozzle member 30 and the operating member 40 (FIG. 1). When the cap 53 is attached, the base part 42 of the operating member 40 exposed to the outside and the barrel part 13 of the container body 10 form a shapely cylindrical body together with the cap 53 as a whole.

A mechanism for dropping a fixed amount of a drug solution by using the eye drops container of the present invention is as follows. When the cap 53 is removed and the whole body is in the upright state, the ball 52 falls down to the bottom groove 51a of the guide member 51 as shown in FIG. 3 (A) so that the nozzle member 30 is prevented from moving and, further, the stem 24 is prevented from being pressed down due to interference of the lower end of the skirt 34 of the nozzle member 30 with the ball 52 even if the operating piece 41 is pressed downward (in the direction of an arrow A). In short, the ball 52 in this state can prevent the open operation of the valve mechanism 20. In contrast, when the whole body is in the inverted state, the ball 52 falls onto the outer flange 33 that is outside the skirt 34 as shown in FIG. 3(B) so that the nozzle member 30 is allowed to move. When the upwardly-open operation (in the direction of an arrow B of FIG. 3(B)) of the operating piece 41 is performed, the elastic tongue piece 44 is bent upward so that the projections 41b and 41b are abutted to the lower surface of the outer flange 33, thereby allowing the stem 24 to be pressed in the axial direction via the nozzle member 30. Thus, it is possible to perform the open operation of the valve mechanism 20 so as to allow the drug solution to be dropped from the drop nozzle 31 for ocular instillation. In short, the ball 52 in the inverted state allows the open operation of the valve mechanism 20, and a forward end of the skirt 34 enters the bottom groove 51a.

When an operating force is eliminated from the operating piece 41, the elastic tongue piece 44 is elastically restored so that the nozzle member 30 and the stem 24 return to the original positions by the spring 28 of the valve mechanism 20. Therefore, every time the operating force is applied repeatedly to the operating piece 41, the fixed amount of the drug solution is discharged from the drop nozzle 31 to realize ocular instillation of a droplet having an appropriate size.

In the foregoing explanation, the inner diameter of the nozzle pore 31a of the drop nozzle 31 may preferably be set to about 1.4 mm for the purpose of dropping the drug solution as an appropriate droplet. Also, in order to suppress the drug solution remaining in the pore 24a of the stem 24 and the nozzle pore 31a of the drop nozzle 31 to a minimum amount after the drug solution dropping, it is preferable to suppress a whole length of the stem 24 and the drop nozzle 31 to a shortest possible length. Therefore, the length of the outer cylinder 32 is set to that for projecting to the upper surface of the operating piece 41 for the purpose of enabling comfortable ocular instillation with the short drop nozzle 31. An inner diameter of the outer cylinder 32 may preferably be set to 5.0 mm or more in order to prevent the droplet from the drop nozzle 31 from sticking to the inner wall due to a surface tension. Also, in order to prevent a harmfully large amount of dropping, it is preferable to suppress a flow rate of the drug solution to be supplied to the drop nozzle 31 to a small value by keeping the diameters of the pores 24b and 24b of the stem 24 as small as possible.

In order to achieve good drainage after dropping the drug solution, the nozzle member 30 may preferably be molded integrally from a water repelling material such as an olefin resin such as polypropylene and polymethylpentene and a fluorine resin. The same applies to the stem 24.

Figure 5:
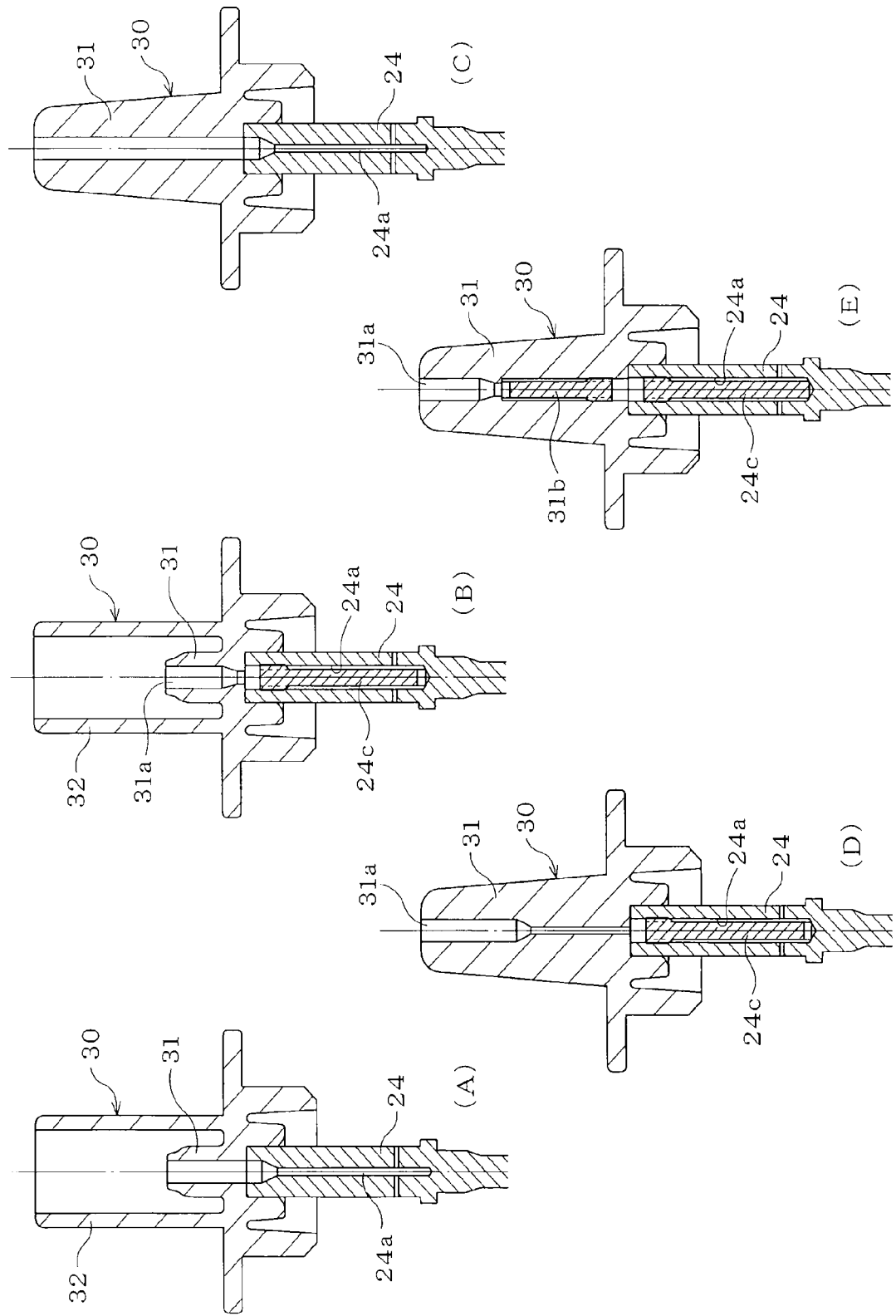
[FIG. 5] A sectional view showing another embodiment of the nozzle mechanism.
Figure 6:
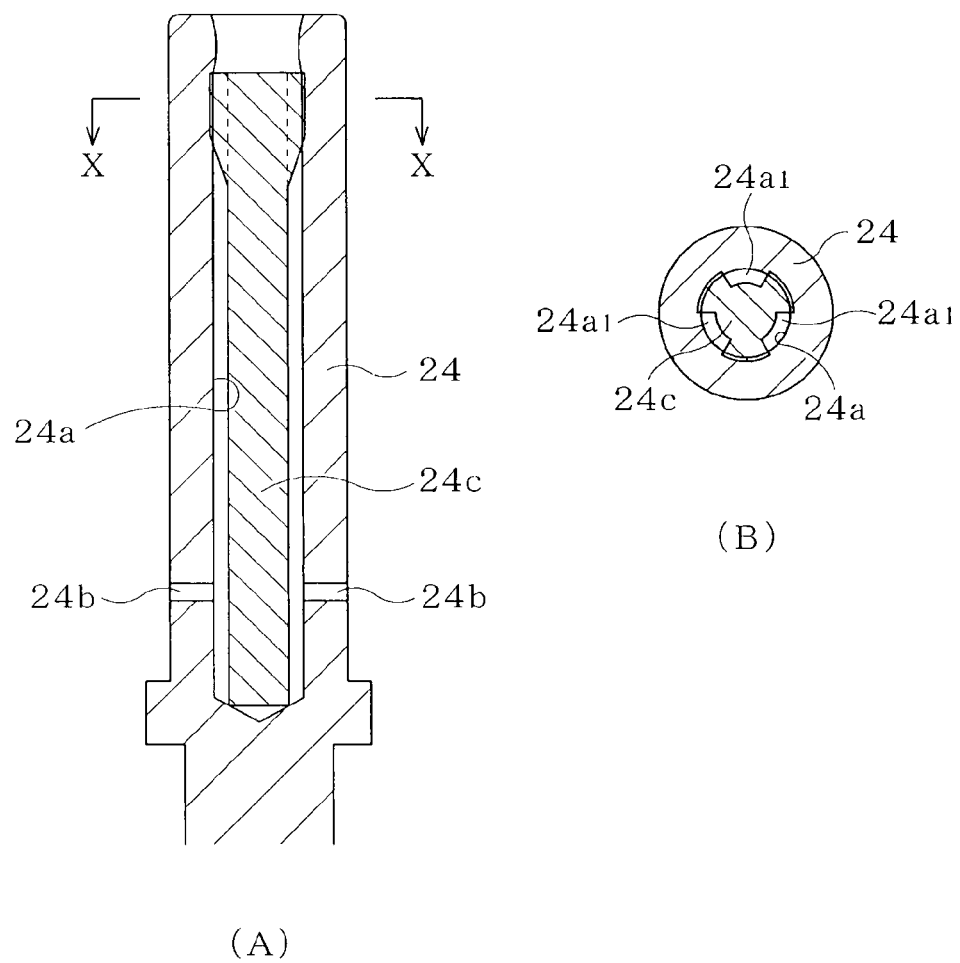
[FIG. 6] An enlarged view for explaining a main part of FIG. 5.

As described in the foregoing, it is preferable to suppress the drug solution remaining in the nozzle pore 31a of the drop nozzle 31 and the pore 24a of the stem 24 to a minimum amount after the drug solution is dropped. Accordingly, another embodiment of the nozzle mechanism different from the above-described one will be explained. For example, a diameter of the pore 24a of the stem 24 is reduced in FIG. 5(A), and a plug body 24c is fitted into the pore 24a in FIG. 5(B). In FIG. 5(B), the nozzle pore 31a of the drop nozzle 31 is reduced in diameter at the stem 24 side in a tapered fashion. As shown in FIG. 6(A) which is an enlarged sectional view showing a main part of FIG. 5(B), the plug body 24c is a stick material having a smaller diameter than the pore 24a and forms a spline by increasing a diameter of one end part close to the drop nozzle 31, and flow paths 24a1, 24a1, and the like each in the form of a recessed groove extending in the axial direction are formed between the plug body 24c and the inner surface of the pore 24a when the plug body 24c is pressed into the pore 24a via the large diameter part as shown in FIG. 6(B) which is a sectional view taken along the line X-X and viewed in a direction of the arrows of FIG. 6(A).

Also, after omitting the outer cylinder 32 by lengthening the drop nozzle 31, the diameter of the pore 24a of the stem 24 may be reduced (FIG. 5(C)); the plug body 24c may be fitted into the pore 24a of the stem 24 by reducing an inner diameter of a part of the nozzle pore 31a except for the tip part (FIG. 5(D)); or a plug body 31b may be fitted into the part of the nozzle pore 31a except for the tip part (FIG. 5(E)). The plug body 24c of FIGS. 5(D) and (E) may have a shape same as that shown in FIG. 6, and the plug body 31b of FIG. 5(E) may be in conformity with that shown in FIG. 6.

Figure 7:
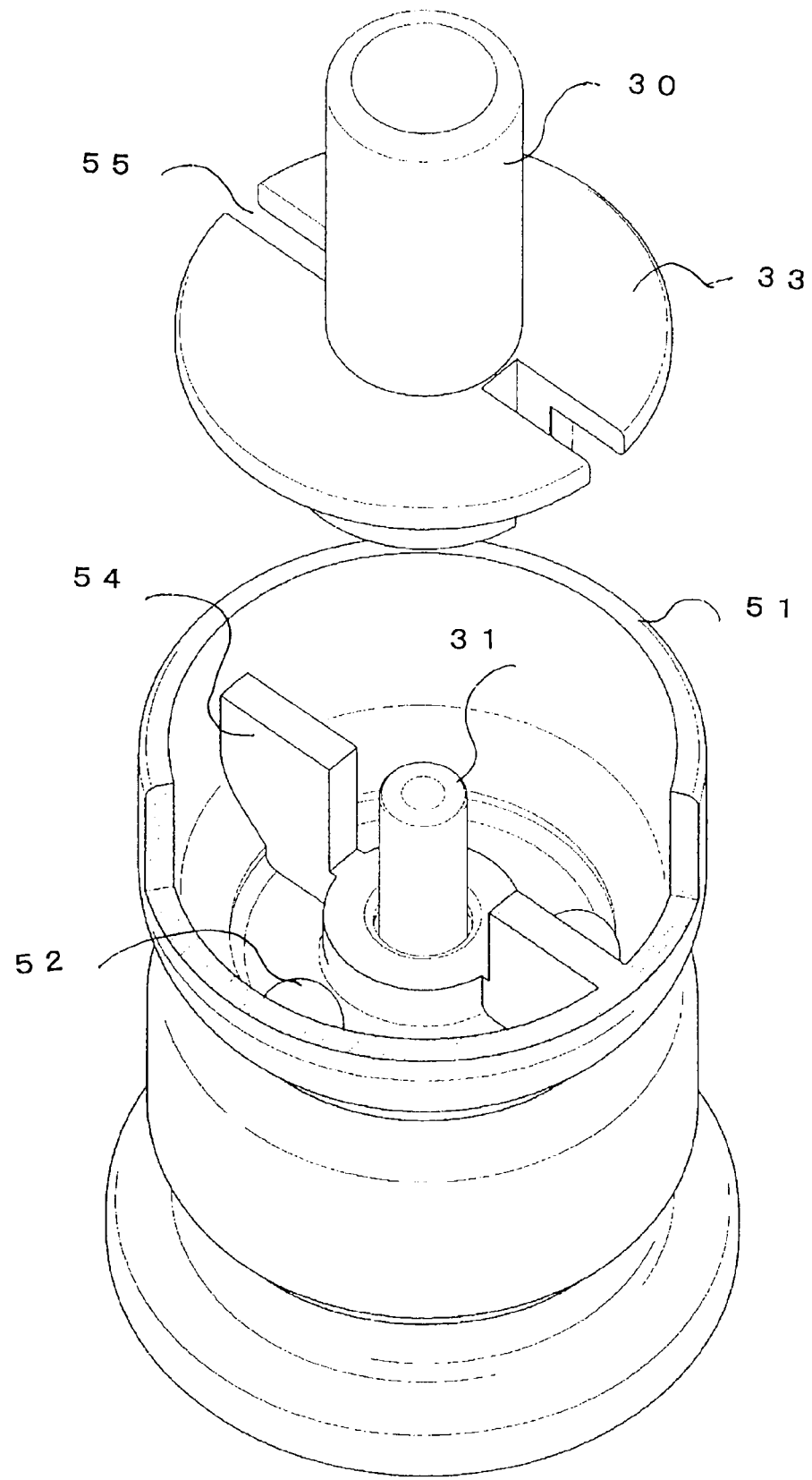
[FIG. 7] A perspective view showing another embodiment of the guide member.

As another mode of the guide member 51, a structure shown in FIG. 7 wherein the bottom groove 51a of the guide member 51 is divided into a plurality of sections and the ball 52 is contained in each of the sections will be described as one example. In this mode, partition walls 54 are provided in the bottom groove 51a in the guide member 51. The outer flange 33 is provided with slits 55 corresponding to the partition walls 54, so that the partition walls 54 do not interfere with the movement of the outer flange 33. With such structure, a so-called erroneous operation prevention function by which the operating piece 41 cannot be pressed down in the upright state is improved. That is to say, it is possible to prevent the erroneous operation by the ball 52 contained in the bottom groove 51a in the structure shown in FIG. 1 and the like, but the operation can be allowed even when an angle is about 45° when the number of balls is small such as one. In contrast, the plurality of balls 52 reliably prevent the erroneous operation of the operating piece 41 when the bottom groove 51a is divided into the plurality of sections.

OPERATION OF THE INVENTION

According to the above-described structure of the invention, the guide member contained in the operating member guides the nozzle member in the axial direction, and the ball contained in the guide member falls into the ring-like bottom groove of the guide member in the upright state to prevent the open operation of the valve mechanism and falls down on the outer flange of the nozzle member in the inverted state to allow the open operation of the valve mechanism. In short, it is possible to perform the open operation of the valve mechanism only in the inverted state, and the valve mechanism is prevented from being erroneously operated in the upright state. Also, the ball in the bottom groove in the upright state is engaged with the lower end of the skirt of the nozzle member to prevent the open operation of the valve mechanism by inhibiting the movement of the nozzle member, and the ball falling down on the outer flange outside the skirt in the inverted state allows the open operation of the valve mechanism without preventing the movement of the nozzle member. The valve mechanism drives the nozzle member via the operating piece of the operating member and presses the stem in the axial direction via the nozzle member for the open operation. When the open operation is performed, the valve mechanism allows the fixed amount of the drug solution to be discharged to the drop nozzle of the nozzle member via the hollow stem, so that the drug solution is dropped as a droplet from the drop nozzle.

In the upright state, the operating piece of the operating member is prevented from moving in the operating direction when the movement of the nozzle member is prevented. That is to say, the operating member does not require any particular member to be provided therewith for limiting the movement of the operating piece, and only the obliquely upward operating piece and the drop nozzle penetrating through the operating piece project above the operating member. Also, since the guide member containing the ball is collectively contained in the operating member in addition to the outer flange and the skirt of the nozzle member, it is possible to form the operating member that is approached to the eye for ocular instillation into a small and neat shape, thereby realizing remarkably good usability.

Also, in the case of forming on the operating piece the axially symmetrical projections for pressing the outer flange, it is possible to correctly drive the stem of the valve mechanism via the nozzle member in the axial direction. The axially symmetrical projections never incline the nozzle member improperly and are free from raising the risk of applying an unnecessary bending stress to the stem.

Further, by providing the cap to the operating member, it is possible to cover the drop nozzle of the nozzle member and the operating piece of the operating member as well as to form the shapely cylindrical body together with the container body. In the operating member, it is preferable to form the base part to be fitted into the container body into the cylindrical shape having the same diameter as the barrel part of the container body, and it is preferable to form the cap into the bottomed cylindrical shape having the same diameter.

Further, it is preferable that the drop nozzle enables formation and dropping of a droplet of the drug solution that has an appropriate size of a volume of about 40 μl, and the inner diameter of the nozzle pore at the tip part may preferably be set to about 1.4 mm. In turn, it is preferable to suppress the drug solution remaining in the nozzle pore to a smallest possible amount since the solution is retained in the nozzle pore until the next use. Therefore, it is preferable to shorten the total length of the nozzle pore of the drop nozzle and the pore for drug solution discharge of the stem of the valve mechanism communicated with the nozzle pore, and the inner volume may preferably be reduced by reducing the inner diameter of the part except for the tip part of the drop nozzle, by fitting the plug body having the flow paths for drug solution discharge, or the like. Also, it is preferable to prevent a harmfully large amount of dropping by reducing the flow rate of the drug solution to be supplied from the container body to the drop nozzle.

The invention claimed is:

1. An eye drops container comprising:
a container body being filled with a drug solution along with a pressurized gas and including a valve mechanism for discharging a fixed amount of drug solution;
a nozzle member coupled with a stem for open operation of the valve mechanism and including a drug solution drop nozzle;
an operating member including an operating piece and attached to the container body;
a guide member contained in the operating member and guiding the nozzle member in an axial direction; and
a ball contained in the guide member,
wherein the nozzle member includes an outer flange for suspending a skirt on the lower surface thereof;
wherein the guide member includes a bottom groove into which the forward end of the skirt enters, the bottom groove being in the form of a ring; and
wherein the ball falls into the bottom groove in an upright state to block the open operation of the valve mechanism and falls onto the outer flange in an inverted state to permit the open operation of the valve mechanism.

2. The eye drops container according to claim 1, wherein axially symmetrical projections for pressing the outer flange are formed on the operating piece.

3. The eye drops container according to claim 1, wherein the operating member includes a detachable cap for containing the nozzle member and the operating member.

4. The eye drops container according to claim 1, wherein the drop nozzle suppresses the drug solution remaining inside to a minimum amount.

5. The eye drops container according to claim 1, wherein the bottom groove of the guide member is divided into a plurality of sections by partition walls, and a ball is contained in each of the plurality of sections.

6. The eye drops container according to claim 5, wherein the outer flange includes slits corresponding to the partition walls so that the outer flange freely moves in a vertical direction with respect to the partitions provided in the guide member.

* * * * *